United States Patent [19]

Woiszwillo

[11] Patent Number: 5,578,709
[45] Date of Patent: Nov. 26, 1996

[54] MACROMOLECULAR MICROPARTICLES AND METHODS OF PRODUCTION

[75] Inventor: James E. Woiszwillo, Milford, Mass.

[73] Assignee: Middlesex Sciences, Inc., Norwood, Mass.

[21] Appl. No.: 206,456

[22] Filed: Mar. 4, 1994

Related U.S. Application Data

[63] Continuation-in-part of Ser. No. 28,237, Mar. 9, 1993.

[51] Int. Cl.[6] .............................. C07K 17/02; C07K 1/00; C08H 1/02; G01N 33/544
[52] U.S. Cl. ...................... 530/410; 530/350; 530/402; 530/812; 436/523; 436/528
[58] Field of Search .................................. 530/350, 402, 530/409, 410, 810, 811, 812, 813; 436/518, 523, 528, 529, 535

[56] References Cited

U.S. PATENT DOCUMENTS

| | | | |
|---|---|---|---|
| 3,137,631 | 6/1964 | Soloway | 424/491 |
| 3,663,687 | 5/1972 | Evans | 424/1.25 |
| 3,838,007 | 9/1974 | van Velzen | 435/96 |
| 4,115,534 | 9/1978 | Ithakissios | 436/500 |
| 4,147,767 | 4/1979 | Yapel, Jr. | 424/499 |
| 4,169,804 | 10/1979 | Yapel | 252/62.53 |
| 4,377,567 | 3/1983 | Geho | 424/1.21 |
| 4,794,000 | 12/1988 | Ecanow | 424/457 |
| 4,822,535 | 4/1989 | Ekman et al. | 264/4.3 |
| 4,824,678 | 4/1989 | Lindahl et al. | 424/473 |

(List continued on next page.)

FOREIGN PATENT DOCUMENTS

| | | |
|---|---|---|
| 0106495A3 | 4/1984 | European Pat. Off. . |
| 0106495 | 4/1984 | European Pat. Off. . |
| 0414223A2 | 2/1991 | European Pat. Off. . |
| 0414223 | 2/1991 | European Pat. Off. . |
| 63-077821 | 4/1988 | Japan . |
| 86223230 | 4/1988 | Japan . |
| 2002319 | 2/1979 | United Kingdom . |
| 2079937 | 1/1982 | United Kingdom . |
| WO93/14110 | 7/1993 | WIPO . |

OTHER PUBLICATIONS

Carrell, S., "Novel Systems for Drug Delivering Biotechnology Drugs Explored," *Genetic Engineering News*, pp. 2 and 10 (Feb. 1993).

Danishefsky, S., "Catalytic Antibodies and Disfavored Reactions," *Science* 259:469–470 (1993).

Farrugia, et al., "Studies on the Procurement of Coagulation Factor VIII: Selective Precipitation of Factor VII with Hydrophilic Polymers," *Thromb. Haemostas* 51(3):338–342 (1984).

Harris, W. J. and Emery, S., "Therapeutic Antibodies—The Coming of Age," *TibTech* vol. 11, Feb. 1993 pp. 42–44.

Madhusudhan, R., et al., "Modification of Enzyme Activity in Reversed Micelles Through Clathrate Hydrate Formation," *Biotechnol. Prog.* 6:465–471 (1990).

(List continued on next page.)

*Primary Examiner*—John L. LeGuyader
*Assistant Examiner*—Nancy J. Degen
*Attorney, Agent, or Firm*—Jones & Askew

[57] ABSTRACT

A macromolecular microparticle composition formed by dehydrating an aqueous macromolecule solution and crosslinking the dehydrated macromolecules with a crosslinking agent while in a liquid phase or with heat. Preferably, the dehydrating agent is a polymer mixture of polyvinylpyrrolidone and polyethylene glycol, the crosslinking reagent is glutaraldehyde, and the macromolecule is a protein, most preferably an immunoglobulin. Methods of use for research, diagnostics and therapeutics are also provided.

18 Claims, 2 Drawing Sheets

U.S. PATENT DOCUMENTS

| | | | |
|---|---|---|---|
| 4,863,972 | 9/1989 | Itagaki et al. | 521/141 |
| 4,904,592 | 2/1990 | Freeman et al. | 435/183 |
| 4,931,284 | 6/1990 | Ekman et al. | 424/450 |
| 4,963,367 | 10/1990 | Ecanow | 424/485 |
| 5,141,738 | 8/1992 | Rasor et al. | 424/9.52 |
| 5,223,263 | 6/1993 | Hostetler et al. | 424/450 |
| 5,264,618 | 11/1993 | Felgner et al. | 560/244 |

OTHER PUBLICATIONS

Phillips, J. B., et al., "Protein Recovery from Reversed Micellar Solutions through Contact with a Pressurized Gas Phase," *Biotechnol. Prog.* 7:43–48 (1991).

Suelter, C. H., *A Pratical Guide to Enzymology*, John Wiley & Sons (1986) pp. 78–87.

Taylor, R., "Expanding Applications in the Food Industry for Immobilized Enzymes," *Genetic Eng. News* (Feb. 1993) p. 5.

Waldmann, T. A., "Monolclonal Antibodies in Diagnosis and Theraphy," *Science* 252:1657–1662 (1991).

Whitman, J. and Scott Marsh, "Purified Viruses and Viral Proteins," (Name of Journal Unknown).

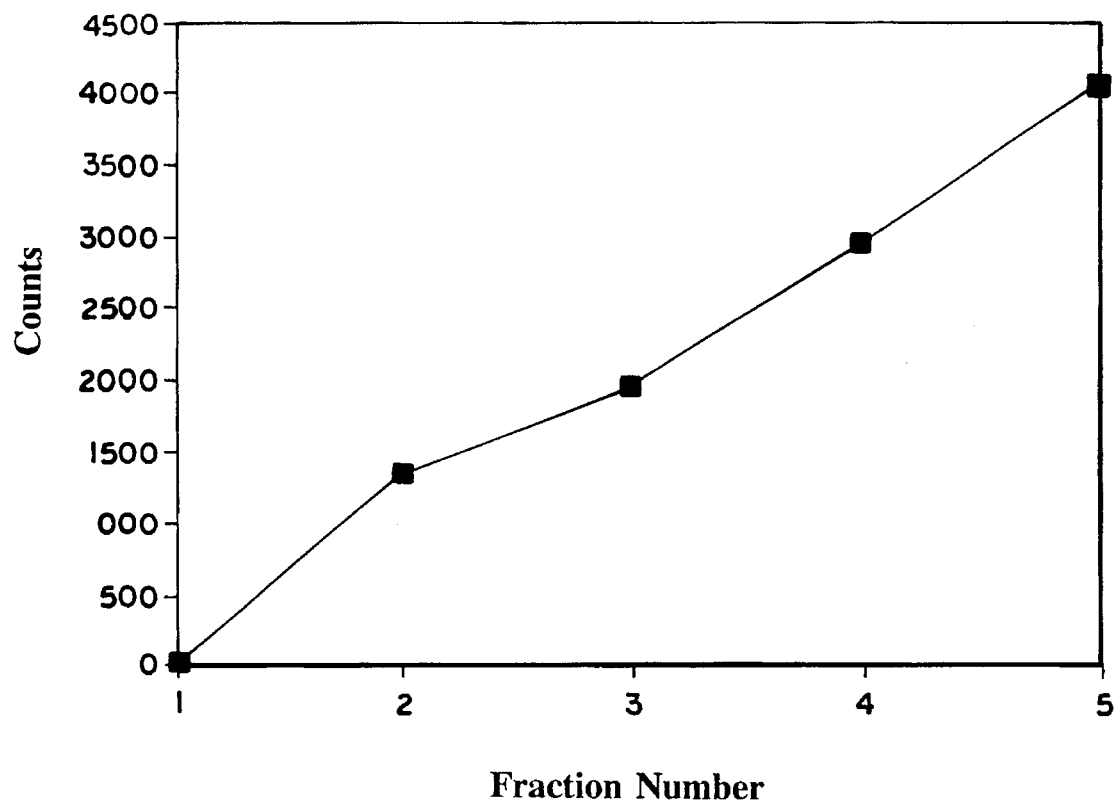
Fig_1

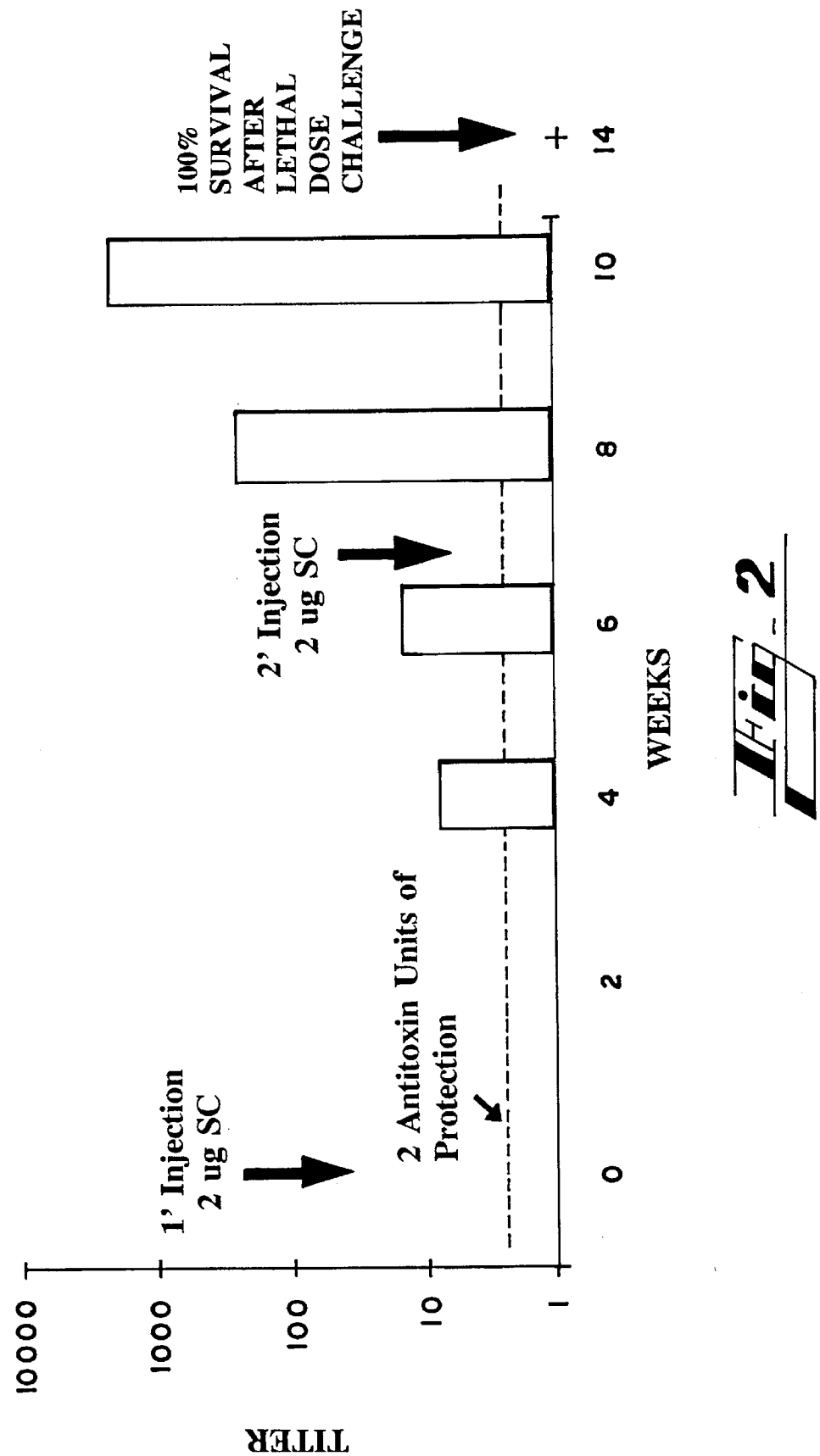

MACROMOLECULAR MICROPARTICLES AND METHODS OF PRODUCTION

CROSS-REFERENCE TO RELATED APPLICATION

This is a continuation-in-part of U.S. patent application Ser. No. 08/028,237, filed Mar. 9, 1993, by James E. Woiszwillo, now pending.

BACKGROUND OF THE INVENTION

Microparticles, microspheres, and microcapsules, referred to herein collectively as "microparticles" are solid particles having a diameter of less than one millimeter, more preferably less than 100 microns, which can be formed of a variety of materials, including synthetic polymers, proteins, and polysaccharides. Microparticles have been used in many different applications, primarily separations, diagnostics, and drug delivery.

The most well known examples of microparticles used in separations techniques are those which are formed of polymers of either synthetic or protein origin, such as polyacrylamide, hydroxyapatite or agarose, which are used to separate molecules such as proteins based on molecular weight and/or ionic charge, or by interaction with molecules chemically coupled to the microparticles.

In the diagnostic area, microparticles are most frequently used in the form of a microparticle which serves to immobilize an enzyme, substrate for the enzyme, or labelled antibody, which is then interacted with a molecule to be detected, either directly or indirectly.

In the controlled drug delivery area, microparticles are formed in mixture with molecules to be encapsulated within the microparticles, for subsequent release. A number of different techniques are routinely used to make these microparticles from synthetic polymers, natural polymers, proteins and polysaccharides, including phase separation, solvent evaporation, emulsification, and spray drying.

Microparticles may also be created as a by-product of separations technology, for example, in some precipitation processes, such as precipitation with ammonium sulfate. However, in these cases, the precipitate is collected and compacted by centrifugation and/or filtration, then redissolved in a solvent to separate out the precipitating agent, the salt, from the molecule precipitated with the salt. Accordingly, the microparticles are unstable and function solely as an intermediate product, not as the end product per se.

Spherical beads or particles have been commercially available as a tool for biochemists for many years. For example, antibodies are often conjugated to beads to create relatively large particles specific for particular ligands. The large antibody-coated particles are routinely used to crosslink receptors on the surface of a cell for cellular activation, are bound to a solid phase for immunoaffinity purification, or are used to deliver a therapeutic agent that is slowly released over time at a distant site, using tissue or tumor-specific antibodies conjugated to the particles to target the agent to the desired site.

The most common method of covalently binding an antibody to a solid phase matrix is to activate a bead with a chemical conjugation agent and then bind the antibody to the activated bead. The use of a synthetic polymeric bead rather than a protein molecule allows the use of much harsher activation conditions than many proteins can sustain, is relatively inexpensive, and often yields a linkage that is stable to a wide range of denaturing conditions. A number of activated beads are commercially available, all with various constituents and sizes. Beads formed from synthetic polymers such as polyacrylamide, polyacrylic, polystyrene, or latex are commercially available from numerous sources such as Bio-Rad Laboratories, Richmond, Calif. and LKB Produkter, Stockholm, Sweden. Bead formed from natural macromolecules and particles such as agarose, crosslinked agarose, globulin, deoxyribose nucleic acid, and liposomes are commercially available from sources such as Bio-Rad Laboratories, Richmond, Calif.; Pharmacia, Piscataway, N.Y.; and IBF (France). Beads formed from copolymers of polyacrylamide and agarose are commercially available from sources such as IBF and Pharmacia. Magnetic beads are commercially available from sources such as Dynal Inc., Great Neck, N.Y.

As the wide variety of materials and applications indicates, there is an on-going need for development of new methods for making and using microparticles, particularly those that can be adapted for use in the separations, diagnostic and drug delivery area, rather than in just one application.

It is therefore an object of the present invention to provide stable microparticles and a process for making the microparticles that is relatively simple, rapid, and inexpensive.

It is a further object of the present invention to provide microparticles that have a high affinity and specificity for a target molecule.

It is a further object of the present invention to provide microparticles that are not absorbed when administered in vivo.

It is a further object of the present invention to provide microparticles for use in separations techniques, especially affinity chromatography.

It is a further object of the present invention to provide microparticles for use in medical and diagnostic applications, such as target-specific drug delivery and histopathological or in vivo tissue or tumor imaging.

SUMMARY OF THE INVENTION

Microparticles, methods of production, and methods of use thereof are provided based on methods for "dehydrating" macromolecules such as proteins, carbohydrates, polysaccharides, nucleic acids, viruses, virus particles, organic or inorganic synthetic pharmaceutical drugs, or any mixture thereof; and forming the macromolecule microparticles by incubation in the presence of heat or "crosslinking" the macromolecules while in a liquid phase. The macromolecules are dehydrated using an agent that effectively dehydrates all but "pockets" of macromolecules that remain dissolved or suspended in an aqueous phase, for example, by dehydration with an agent such as ammonium or sodium salts, organic solvents, high concentrations of linear or branch polymers, divalent ions such as zinc, or chaotropic agents. The macromolecules can consist of drugs, biologically active molecules, carrier molecules, affinity molecules or mixtures thereof.

Microparticles are formed by incubation of the dehydrated macromolecules for a predetermined length of time at a temperature greater than room temperature. Alternatively, at various temperatures, the macromolecules are crosslinked to form microparticles using a crosslinking agent such as glutaraldehyde or other agents such as amines, multivalent ions, and multifunctional molecules that have an "affinity"

for specific reactive groups on the macromolecule being crosslinked.

The microparticles are then separated from the dehydration agent and excess crosslinking agent, if present, by separation methods such as filtration or centrifugation. The microparticles can then be washed with a quenching reagent that binds to any unreacted binding sites on the crosslinking agents to effectively reduce any subsequent non-specific binding of the microparticle when reacted with a target molecule.

The microparticles are useful for a wide variety of separations, diagnostic, therapeutic and research purposes.

Specific examples are described below in which the microparticles are formed of (1) proteins such as antibodies that have been dehydrated with a high concentration of a linear polymer mixture containing polyvinylpyrrolidone and polyethyleneglycol which were then crosslinked with glutaraldehyde; (2) polysaccharides such as alginate mixed with biologically active molecules that have been dehydrated with a high concentration of a linear polymer mixture containing polyvinylpyrrolidone and polyethyleneglycol and crosslinked with multivalent ions such as polyaminoacids or divalent cations; (3) proteins such as albumin, which are carriers for pharmaceutical drug molecules, that are crosslinked with glutaraldehyde following dehydration of the protein mixture using ammonium or sodium sulfate; (4) peptide hormones such as insulin, crosslinked with glutaraldehyde following dehydration with a mixture of polyvinylpyrrolidone and polyethylene glycol; and (5) proteins such as albumin that are dehydrated with a linear polymer mixture containing polyvinylpyrrolidone and polyethyleneglycol and incubated in the presence of heat.

BRIEF DESCRIPTION OF THE DRAWINGS

FIG. 1 is a graph showing counts per minutes (counts) of bound radioactive carcinogenic embryonic antigen versus anti-carcinogenic embryonic antigen microparticle concentration.

FIG. 2 is a graph showing antibody titer versus weeks after immunization with primary and secondary doses of tetanus toxoid particles.

DETAILED DESCRIPTION OF THE INVENTION

Microparticles, methods of production, and kits are provided for diagnostic, therapeutic and research use. The microparticles are crosslinked macromolecular structures having a large surface area. The macromolecules forming the microparticles include, but are not limited to, proteins, carbohydrates, polysaccharides, nucleic acids, viruses, virus particles, organic or inorganic synthetic pharmaceutical drugs, or mixtures thereof that can be crosslinked in a liquid phase under conditions of dehydration.

Formation of Polymer Microparticles

The microparticle is formed by incubating macromolecules in solution or in liquid phase in the presence of a dehydrating agent and heat or a crosslinking agent for a sufficient amount of time to form particles. The macromolecule is first dissolved in an aqueous solvent, then either the macromolecule solution is added to the dehydrating agent or the dehydrating agent is added to the macromolecule solution, preferably the latter. The dehydrated macromolecule solution is then preferably heated for a predetermined length of time for the formation of microparticles. Alternatively, a crosslinking agent is added to the dehydrated macromolecule solution for microparticle formation at various temperatures. The resulting microparticles are then separated from any unreacted components present in the incubation mixture by physical separation methods well known to those skilled in the art.

Macromolecule

The macromolecule forming the microparticle is any molecule capable of being crosslinked in liquid phase. Most preferably, the macromolecule is a biomolecule such as a protein, carbohydrate, polysaccharide, nucleic acid molecule, virus, virus particle, or a mixture thereof. The macromolecule can also be a natural or synthetic pharmaceutical compound that is capable of being crosslinked. It will be understood by those skilled in the art that a compound incapable of being crosslinked can be formed into a microparticle by incorporation of the compound into a carrier molecule that is then crosslinked in accordance with the methods provided herein. It will be further understood by those skilled in the art that the macromolecule can also be a portion of a molecule having the requisite activity to bind or interact with a ligand, such as, for example, a peptide, a single-stranded segment of a double-stranded nucleic acid molecule, or a virus particle. It will also be understood by those skilled in the art that the term "macromolecule" includes a plurality of macromolecules and includes combinations of different macromolecules such as a combination of a pharmaceutical compound and an affinity molecule for targeting the pharmaceutical compound to a tissue, organ or tumor requiring treatment.

It will be further understood by those skilled in the art that an affinity macromolecule can be either the receptor portion or the ligand portion of a receptor-ligand interaction. Examples of ligands that interact with other biomolecules include viruses, bacteria, polysaccharides, or toxins that act as antigens to generate an immune response when administered to an animal and cause the production of antibodies.

The concentration of macromolecule in the incubation mixture is preferably between 0.1 and 100 mg/mL, depending on the incubation conditions.

Labelled Macromolecule

The macromolecule can be labelled with a detectable label. The various types of labels and methods of labelling proteins and nucleic acid molecules are well known to those skilled in the art. It will be understood by those skilled in the art that a magnetic substance, such as a metal, is included within the definition of the term label. For example, the macromolecule can be labelled with a metallic substance, such as a metal, so that the microparticles can be separated from other substances in a solution with the aid of a magnetic device.

Several other specific labels or reporter groups are set forth below.

For example, the label can be a radiolabel such as, but not restricted to, $^{32}P$, $^{3}H$, $^{14}C$, $^{35}S$, $^{125}I$, or $^{131}I$. A $^{32}P$ label can be conjugated to a protein with a conjugating reagent or incorporated into the sequence of a nucleic acid molecule by nick-translation, end-labelling or incorporation of labelled nucleotide. For example, a $^{3}H$, $^{14}C$ or $^{35}S$ label can be incorporated into a nucleotide sequence by incorporation of a labelled precursor or by chemical modification, whereas an $^{125}I$ or $^{131}I$ label is generally incorporated into a nucleotide sequence by chemical modification. Detection of a label can be by methods such as scintillation counting, gamma ray spectrometry or autoradiography.

The label can also be a Mass or Nuclear Magnetic Resonance (NMR) label such as, for example, $^{13}$C, $^{15}$N, or $^{19}$O. Detection of such a label can be by Mass Spectrometry or NMR.

Dyes, chemiluminescent agents and fluorogens can also be used to label the macromolecule. Examples of dyes useful for labelling nucleic acids include ethidium bromide, actidines, propidium and other intercalating dyes, and 4',6'-diamidino-2-phenylindole (DAPI) (Sigma Chemical Company, St. Louis, Mo.) or other proprietary nucleic acid stains. Examples of fluorogens include fluorescein and derivatives, phycoerythrin, allo-phycocyanin, phycocyanin, rhodamine, Texas Red or other proprietary fluorogens. The fluorogens are generally attached by chemical modification. The dye labels can be detected by a spectrophotometer and the fluorogens can be detected by a fluorescence detector.

The macromolecule can alternatively be labelled with a chromogen (enzyme substrate) to provide an enzyme or affinity label, or enzyme. For example, the macromolecule can be biotinylated so that it can be utilized in a biotin-avidin reaction which may also be coupled to a label such as an enzyme or fluorogen. The macromolecule can be labelled with peroxidase, alkaline phosphatase or other enzymes giving a chromogenic or fluorogenic reaction upon addition of substrate. For example, additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used.

Recognition sites for enzymes, such as restriction enzyme sites on nucleic acid molecules, can also be incorporated into an macromolecule to provide a detectable label. A label can also be made by incorporating any modified base, amino acid, or precursor containing any label, incorporation of a modified base or amino acid containing a chemical group recognizable by specific antibodies, or by detecting any bound antibody complex by various means including immunofluorescence or immuno-enzymatic reactions. Such labels can be detected using enzyme-linked immunoassays (ELISA) or by detecting a color change with the aid of a spectrophotometer.

Dehydrating Agent

The dehydrating agent is a chemical compound or mixture of compounds capable of diffusing water from the macromolecule to a highly ionic media. Suitable dehydrating agent include neutral salts consisting of the sulfates, sulfites, thiosulfates, phosphates, or halogen salts of alkali metals, ammonium or magnesium; glycine; water soluble organic solvents such as ethanol; water soluble nonionizable linear or branched polymers of high molecular weight; metal ions such as zinc; organic cations such as 2-ethoxy-6,9-diaminoacridine lactate; small anions; and polyanions such as polyphosphates and polyacrylic acid.

Preferably, the dehydrating agent is a mixture of two or more soluble, linear polymers such as polyvinylpyrrolidone and polyethylene glycol. Such a polymer mixture may be prepared in accordance with the methods set forth in co-pending U.S. patent application Ser. No. 07/817,610 filed Jan. 7, 1992 by James E. Woiszwillo, or PCT Patent Application No. US93-00073, filed Jan. 7, 1993 by James E. Woiszwillo, both of which are incorporated herein by reference. It will be understood by those skilled in the art that other soluble, linear polymers, such as dextran, nonylphenol-ethoxylates, polyvinyl alcohol, and mixtures thereof could be used in addition to PVP and PEG or in place of either PVP or PEG.

PVP is a non-ionogenic, hydrophilic polymer having a mean molecular weight ranging from approximately 10,000 to 700,000 and the chemical formula $(C_6H_9NO)_n$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)_nH$.

Dextran is a term applied to polysaccharides produced by bacteria growing on a sucrose substrate. Native dextrans produced by bacteria such as *Leuconostoc mesenteroides* and *Lactobacteria dextranicum* usually have a high molecular weight.

Nonylphenol-ethoxylates (NPEs) are a class of long chained compounds often used as surfactants. They are usually derivatized to meet the desired solubility requirements.

Polyvinyl alcohol (PVA) is a polymer prepared from polyvinyl acetates by replacement of the acetate groups with hydroxyl groups and has the formula $(CH_2CHOH)_n$. Most polyvinyl alcohols are soluble in water.

PEG, dextran, PVA and PVP are commercially available from chemical suppliers such as the Sigma Chemical Company (St. Louis, Mo.). NPEs require custom synthesis and can be ordered from special chemical producers.

Most preferably, the dehydrating agent is polymer mixture containing an aqueous solution of PVP having a molecular weight between 10,000 and 360,000, most preferably 40,000 and PEG having a molecular weight between 200 and 35,000. PVP having a molecular weight of 40,000 and PEG having a molecular weight of 3500 is preferred. Alternatively, PVP having a molecular weight of 360,000 is preferred for obtaining microparticles having uniform size. Preferably, the PVP is dissolved in an acetate buffer and PEG is added to the aqueous PVP solution. The concentration of each polymer is preferably between 1 and 40 g/100 ml depending of the molecular weight of each polymer. Most preferably, the concentration of each polymer is 24 g/100 ml or 24%. Equal concentrations of PVP and PEG generally provide the most favorable polymer matrix for the formation of a polymer microparticle. The volume of polymer added to the macromolecule varies depending on the size and quantity of the macromolecule. Preferably, three volumes of the polymer mixture are added to one volume of a solution containing the macromolecule.

Incubation Conditions Using Heat

Microparticles are formed by incubation of the macromolecule and dehydrating agent mixture at a temperature greater than room temperature for a predetermined length of time. Preferably, the mixture is incubated in a water bath at a temperature greater than or equal to 37° C. and less than or equal to 80° C. for between approximately 5 minutes and 2 hours. Most preferably, the mixture is incubated for 15–30 minutes at a temperature between 50° C. and 70° C.

Microparticle size can be controlled by adjusting the incubation conditions. For example, incubation temperatures can be increased gradually or incrementally from room temperture to the desired elevated incubation temperature or overall incubation time can be increased. In addition, the amount of microparticle aggregation can be controlled by varying the concentration, volume, or composition of the dehydrating agent.

CrossLinking Reagent

Microparicles are alternatively formed by the addition of a crosslinking reagent to crosslink the dehydrated macromolecule. The crosslinking reagent is a bi- or multi-functional chemical reagent that physically links the macromolecules, and, in some cases, the dehydrating agent. Examples of suitable crosslinking agents include dialdehydes or other agents such as amines, multivalent ions, and multifunctional molecules that have an "affinity" for specific reactive groups on the macromolecule being crosslinked.

In the preferred embodiment, the crosslinking agent covalently connects the macromolecules into a stable three-dimensional structure. Most preferably, the crosslinking agent is a bifunctional reagent such as glutaraldehyde; p,p'-difluoro-m,m'-dinitro diphenyl sulphone; hexamethylene diisocyanate; n,n'-(1,3-Phenylene)-bis-maleimide; n,n'-ethylene-bis-iodoacetamide; 3,6-bis-(mecurimethyl)-dioxan; bis-diazobenzidine; Woodward's K; bis-oxiranes; dimethyl adipimidate; dimethyl suberimidate; diethyl malonimidate; phenol-2,4-disulphonyl-chloride; divinylsulphone; and carbodiimides.

Most preferably, the crosslinking agent is a dialdehyde such as glutaraldehyde which forms a Schiff base with primary amines, which on reduction with borohydride give stable secondary amines under mild conditions.

An example of another type of crosslinking agent are the N-substituted maleimides which are specific for sulphydryl groups under mild conditions. Several N-aryl and N-alkyl-bis-maleimides are commercially available, including azophenyldimaleimide. These are insoluble in water and are generally added in stoichiometric amounts as a solid to aqueous solution at pH 7 to 8 of the reactants.

Bifunctional alkyl halides react primarily with thiol, imidazole and amino groups. At neutral to slightly alkaline pH the reaction with sulphydryl groups is favored while at higher pH values reaction with amino groups. Other compounds include aryl halides such as 1,5-difluoro-2,4-dinitrobenzene, which are insoluble in water and preferentially react with amino groups and tyrosine phenolic groups, but which will also react with sulphydryl and imidazole groups. Relatively high pH values are required for a rapid reaction. The reagent is generally added as a concentrated acetone solution to an aqueous solution of the reactants and product formation. Isocyanates react with amines to form substitute ureas, with alcohols to form urethanes and with water to give amines and carbon dioxide. At alkaline pH the reaction with amines is preferred. 2,2-dicarboxy-4,4'-azophenyldiisocyanateiswater-soluble and has the advantage that the bridge it forms can be readily cleaved by reduction of the azo group by dithionite. Acylating agents can also be used, such as many of the aliphatic or aromatic dicarboxylic or disulphonic acids that are activated to provide bifunctional acylating agents capable of reacting under mild conditions. The nitrophenylesters of dicarboxylic acids and the aromatic-bis-sulphonyl chlorides are examples. These are insoluble in water and hydrolyse rapidly. The bis-sulphonyl chlorides react with amino groups to form stable suphonamide linkages which can subsequently be cleaved with HBr in glacial acetic acid. Bifunctional imidoesters can also be used which are soluble in water and react with amino groups under mild conditions and with a high degree of specificity. Dimethyl-suberimidate can be used in 0.2M triethanolamine HCl buffer pH 8.5 for three hours at room temperature. The resulting amide is stable to acid hydrolysis, but can be cleaved with ammonia. Vinylsulphones can be used which react primarily with amino groups but, at high pHs, react with carbohydrates, phenols and alcohols.

The concentration of the crosslinking reagent in the incubation mixture should be sufficient to bind all of the active groups of the macromolecule. There is a direct relationship between the concentration of crosslinking agent and the number of microparticles formed after incubation. Generally, more microparticles are formed as the concentration of crosslinking agent in the incubation mixture is increased. Preferably, the concentration of crosslinking agent in the incubation mixture is between approximately 5 and 200 microliters of a 25% solution of glutaraldehyde per milliliter of incubation mixture.

Incubation Conditions for Crosslinking

When using dehydrating agents other than polymer solutions, such as ammonium or sodium salts, organic solvents, divalent ions such as zinc, or chaotropic agents, to form microparticles, one must carefully select the right combination of crosslinking reagent to form the microparticles because of the interaction that can occur between the dehydrating agent and crosslinking agent. Microparticles are formed using ammonium sulfate, glutaraldehyde and protein, but the concentrations of reactants are different than those required for microparticle formation using linear polymers.

Preferably, the dehydrating agent is a polymer solution, where the macromolecule, polymer and crosslinking agent mixture are vigorously mixed together, such as by vortexing, to allow sufficient interaction between the macromolecules, polymers and crosslinking agent, and incubated, while mixing, at room temperature (20° C.), or at a temperature below room temperature, for a sufficient amount of time to allow maximal formation of microparticles. Alternatively, microparticles can be formed utilizing a combination of crosslinking agent and heat.

The length of incubation time is dependent upon the respective concentrations of polymer and affinity molecule and the incubation temperature. Preferably, the polymer mixture and macromolecules are incubated between 30 minutes and 24 hours. Most preferably, the polymer mixture and macromolecules are mixed, by stirring or rocking, for 120 minutes at room temperature and are then placed at 4° C. overnight without mixing.

The pH of the incubation mixture is generally determined by the pH of the dehydrating agent and may be adjusted by adding the appropriate amount of an acidic or basic buffer to either or both dehydrating or macromolecule solutions before they are mixed. Where the dehydrating agent is a linear polymer solution, there is a direct relationship between the size of the microparticle formed at the end of the incubation step and the pH of the incubation mixture. At a higher (more basic) pH, larger microparticle are formed. At a lower pH, the formed microparticle is smaller. The pH of the linear polymer incubation mixture is preferably between approximately 5 and 8.

Quenching of Binding Sites

It will be understood by those skilled in the art that a quenching reagent may be added to the resulting microparticles after incubation to block any unreacted binding sites of the crosslinking reagent in order to reduce subsequent non-specific binding. In the case where the dehydrating agent is a linear polymer solution such as PVP/PEG, suitable quenching reagents are compounds, such as amino acids or albumin, that contain substantial numbers of amino groups. Preferably, the quenching reagent is a solution containing lysine or glycine. Most preferably the quenching reagent is the amino acid glycine in a concentration ranging from 0.1 to 0.5M.

Purification of Microparticles

The formed microparticles are separated from the non-reacted components of the incubation mixture by conventional separation methods well known to those skilled in the art. Preferably, the incubation mixture is centrifuged so that the microparticles fall to the bottom of the centrifuge tube and the non-reacted components remain in the supernatant, which is then decanted. Alternatively, the incubation mixture containing the formed microparticles is filtered so that the microparticles are retained on the filter and the non-reacted components pass through the filter.

Further purification of the microparticles is achieved by washing in an appropriate volume of a washing solution. The preferred washing solution is a buffer, most preferably a phosphate buffered saline solution containing the quenching reagent. Repeated washings can be utilized as necessary.

It will be understood by those skilled in the art that some of the dehydrating agent may be incorporated within the macromolecule structure and actually contribute to the molecular composition of each microparticle.

Microparticle Characteristics

The microparticles formed by the foregoing process can be spherical or non-spherical in shape depending on temperature, polymer size and mixture and protein concentration with one or more active sites present on the surface of each microparticle. The eliptical shape and granularity of the microparticles create a particle having a greater surface area than spherical microparticle beads and allows for the incorporation of a larger number of macromolecules per microparticle than could be achieved with conventional spherical beads.

Furthermore, in the example where microparticles are formed of macromolecules such as immunoglobulin crosslinked with glutaraldehyde in the presence of PVP/PEG, the microparticles are stable at alkaline and acid pH and are not absorbed when administered in vivo.

The microparticles are useful for a wide variety of diagnostic, therapeutic, and research purposes as discussed in more detail below. For example, for in vivo diagnostic purposes, the microparticles can include a macromolecule such as an immunoglobulin or cell receptor labelled with a detectable label. Injection of the labelled microparticle into a patient creates an imaging agent for the diagnosis of a proliferative disorder such as cancer or a tool for the evaluation of the success of a therapeutic agent in reducing the proliferation of a particular adverse cell or organism. For in vitro diagnosis, microparticles containing a macromolecule, such as an immunoglobulin, cell receptor or oligonucleotide probe specific for the cell or organism under investigation, are combined with a test sample, the microparticles are separated from any non-bound components of the sample, and bound molecules are detected by conventional methods. The microparticles are useful as therapeutic agents when the microparticles include a therapeutic drug and are injected into a patient for slow release or targeted delivery of the drug to the site requiring therapy.

The microparticles are also useful for the purification of molecules from a complex mixture, as a reagent for the detection or quantification of a specific molecule, or for the production of molecules, such as antibodies. For example, microparticles containing a macromolecule, such as an immunoglobulin, can be attached to a chromatography column and used in immunoaffinity chromatography to separate a ligand from a complex mixture. Alternatively, microparticles including a labelled macromolecule or a mixture of labelled macromolecules specific for different cells or biomolecules, such as cell receptors, can be used to detect changes in the number of cells or biomolecules in response to a particular test condition using techniques such as flow cytometry. Furthermore, the microparticles can be used as adjuvants for vaccine production wherein antigen-containing microparticles are injected into a research animal, such as a mouse or rabbit, to trigger an enhanced immune response for the production of antibodies to the antigen.

In Vitro Diagnostics

In vitro assays

The microparticles described herein are useful as solid phase particles in an assay, such as an enzyme-linked immunosorbant assay, dot-blot, or Western blot, for the detection of a particular target such as a cell, biomolecule or drug in a biological sample. The microparticles designed for this use are composed of affinity molecules specific for the target molecule. For example, the macromolecule is an immunoglobulin, cell receptor or oligonucleotide probe and is bound to a test tube or microtiter plate.

For detection or quantitation of a target molecule of interest, a sample is combined with a solution containing the microparticles, the macromolecules on the microparticles are reacted with the target molecule, the microparticles are separated from any non-bound components of the sample, and microparticles containing bound molecules are detected by conventional methods. Fluorescently stained microparticles are particularly well suited for flow cytometry analysis in accordance with methods well known to those skilled in the art.

Histopathology

The microparticles described herein are useful as visual probes or markers of pathology in a histological sample. The macromolecules of microparticles designed for this use are specific for biomolecules expressed during a particular pathologic condition and are labelled with a detectable label. For example, the macromolecule is an immunoglobulin, cell receptor or oligonucleotide probe specific for an abnormal cell, such as a rapidly proliferating cell, or pathological organism, for example, a virus.

For detection of a pathogenic condition, a histological sample is combined with a solution containing the microparticles, the labelled macromolecules on the microparticles are reacted with the target molecule of interest, and bound microparticles are detected by detecting the label in accordance with methods well known to those skilled in the art.

In Vivo Diagnostics—Imaging

The microparticles described herein are useful as imaging agents for in vivo localization of a particular molecule, cell type or pathologic condition in a manner similar to that described above with regard to the use of the microparticles for histopathology. The macromolecules on microparticles designed for this use are specific for molecules expressed by a particular cell or pathologic organism and are labelled with a detectable label. For example, the macromolecule is an immunoglobulin, cell receptor or oligonucleotide probe specific for a tumor cell or pathological organism, such as a virus.

The microparticles are used to either detect a pathologic condition or to monitor the success of therapy, such as chemotherapy or surgery to ensure that the size of an abnormal tissue tumor has decreased or has been completely excised. For this use, a patient receives an administration of a microparticle solution, preferably intravenously, the labelled macromolecules on the microparticles are given a sufficient amount of time to localize to the affected organ or region of the body, the macromolecule is reacted with a target molecule expressed by the cell or organism under investigation, and bound microparticles are detected by detecting the label by conventional imaging techniques well known to those skilled in the art, such as x-ray.

Therapeutics-Drug Delivery Systems

The microparticles are useful for therapy when composed of a crosslinked pharmaceutical compound or a crosslinked carrier, such as albumin, containing a therapeutic agent. The microparticle can either provide for the slow release of the agent throughout the body or the microparticle can include an affinity molecule specific for a target tissue, or tumor, and be injected into a patient for targeted delivery of the therapeutic agent, such as an antitumor, antiviral, antibacterial, antiparasitic, or antiarthritic agent, cytokine, hormone, or insulin directly to the site requiring therapy.

Research Applications

The microparticles are also useful as research tools for the purification of a biomolecule from a complex mixture, as a reagent for the detection or quantification of a biomolecule, or for the production of biomolecules, such as antibodies.

For example, microparticles composed of a macromolecule, such as an immunoglobulin, are attached to a chromatography column and used in immunoaffinity chromatography to separate a ligand from a complex mixture. It will be understood by those skilled in the art that microparticle for use in high pressure liquid chromatography should be first attached to a non-compressible solid phase sphere or bead so that the column packing maintains its rigid structure under pressure.

Alternatively, microparticles including a labelled macromolecule or a mixture of labelled macromolecules specific for different cells or cell receptors are used to detect changes in the number of cells or cell surface receptors in response to a particular test condition using techniques such as flow cytometry.

Furthermore, the microparticles are useful adjuvants for antibody production wherein antigen-containing microparticles are injected into an animal, such as a mouse or rabbit, for vaccine production, or a human, to induce immunity to an antigen, to trigger an enhanced immune response for the production of antibodies to the antigen.

Kit for the Production of Microparticles

A kit for the production of microparticles is provided. The kit contains the following reagents: a dehydrating agent and a crosslinking agent. The user of the kit may use the kit for the preparation on custom microparticles wherein the user will supply the macromolecule that will be formed into the microparticles. Alternatively, the kit can contain one or more macromolecules, in solution or lyophilized form, for the preparation of microparticles of interest to the user. The formed microparticles can then be used for research, therapeutics or diagnostics as described above. The kit preferably also contains a buffer, such as phosphate buffered saline, containing a quenching reagent, such as glycine, to block non-specific binding by the crosslinking reagent. A detectable label, or prelabelled macromolecule can also be included with the kit to provide a means for detecting the presence of the microparticle in a sample or patient.

The polymer microparticles and methods described above will be further understood with reference to the following non-limiting examples.

Example 1: Preparation of Microparticles with Gammaglobulin and a Polymer Mixture of Polyvinylpyrrolidone and Polyethylene Glycol and a Stability Analysis Thereof Microparticle Formation Microparticles were formed by combining gammaglobulin, one of five molecular weight preparations (MW 10,000–360,000) of a 5–25% polyvinylpyrrolidone solution, and a constant molecular weight preparation (MW 3500) of a 25% polyethylene glycol solution (both prepared as described below in Example 2) in the presence of glutaraldehyde, at a reaction pH range between 6.9 and 7.75, by the following process. The microparticles were stable in both acidic and basic solutions.

Five polymer mixtures, each containing a different molecular weight preparation of polyvinylpyrrolidone, were prepared as indicated below in Table 1. Twenty microliters of glutaraldehyde (25%, Sigma Chemical Company, St. Louis, Mo.) were added to each polymer mixture. One milliliter of purified goat gammaglobulin (Sigma Chemical Company, St. Louis, Mo.), purified in accordance with the methods described in co-pending U.S. patent application Ser. No. 07/817,610, filed Jan. 7, 1992 by James E. Woiszwillo and PCT Patent Application No. US93-00073, filed Jan. 7, 1993 by James E. Woiszwillo, both of which are incorporated by reference herein, was reacted with each of the five polymer mixtures by vortexing briefly. The reaction solutions were mixed for 40 minutes at 20° C. and then incubated at 4° C. overnight.

All five reaction solutions were restored to 20° C., 100 µl DL-lysine (Sigma Chemical Company, St. Louis, Mo.) was added to each solution, and the solution was mixed for 90 minutes at 20° C.

The solutions were centrifuged at 5000 rpm for 30 minutes at 20° C. The supernatants were decanted and the precipitates resuspended in 1 ml of a buffer solution containing 1.0 ml phosphate buffered saline (PBS) containing 0.2% Tween (Sigma Chemical Company, St. Louis, Mo.).

One hundred microliters of each resuspended precipitate was reacted with 100 µl of a 1:2000 dilution of anti-goat IgG peroxidase conjugate for 15 minutes at 20° C. One ml of the PBS/Tween buffer was added to each reaction mixture and the mixtures were incubated at 42 C. overnight.

The samples were centrifuged, 100 µl of each supernatant was removed from each and reacted with 300 µl TM Blue. The remaining supernatants were carefully decanted and precipitates were resuspended in 1 ml of the PBS/Tween solution.

The resuspended samples were again centrifuged, 100 µl removed and reacted with 300 µl TM Blue, supernatants decanted, and precipitates resuspended in 1 ml PBS/Tween. A 100 µl aliquot of the resuspended precipitate was reacted with 300 µl TM Blue.

The resuspended samples were again centrifuged, 100 µl removed and reacted with 300 µl TM Blue, supernatants decanted, and precipitates resuspended in 1 ml PBS/Tween. A 100 µl aliquot of the resuspended precipitate was reacted with 300 µl TM Blue. The results are shown below in Tables 1 and 2.

TABLE 1

Quantity and Characteristic of Microparticles Formed with Five Different MW Preparations of PVP

| Reaction # | PVP (MW) | Ppt Amt | Particle Characteristics |
|---|---|---|---|
| 1 | 10,000 | 1X | very fine |
| 2 | 24,000 | 2X | very fine |
| 3 | 40,000 | 2X | very fine |
| 4 | 90,000 | 2X | small |
| 5 | 360,000 | 1.5X | small |

TABLE 2

Relative Gammaglobulin Concentration in Supernatant and Precipitate Fractions after Microparticle Formation and Washing

| Reaction # | Sup. 1 | Sup. 2 | Ppt. 2 | Sup. 3 | Ppt. 3 |
|---|---|---|---|---|---|
| 1 | +++++ | ++ | ++ | − | ++ |
| 2 | +++++ | ++ | ++ | + | ++ |
| 3 | +++++ | + | + | − | + |
| 4 | +++++ | + | ++ | − | ++ |
| 5 | +++++ | + | ++ | − | ++ |

The results presented in Table 1 indicate that microparticles were formed for all five solutions containing different molecular weight preparations of PVP in the presence of glutaraldehyde.

The results presented in Table 2 indicate that the gammaglobulin was attached to the microparticles present in the precipitate, even after three washes.

Microparticle Stability Analysis

Three reactions were preformed on the first resuspended precipitate of reaction #3 to analyze the effects of acidic or basic solutions on the stability of the microparticles as follows.

One hundred microliters of the first resuspended precipitate of reaction #3 were placed into three test tubes. Two hundred microliters of deionized water were added to the first tube. Particles were observed. Two hundred microliters of 1N acetic acid were added to the second tube. Particles having the same size as observed in the first tube were observed. Two hundred microliters of 1% Na OH were added to the third tube. Particles having the same size as observed in the first tube were observed.

All three tubes were placed at 4° C. overnight and observed again on the following day. Tubes 1 and 2 did not change. Tube 3 appeared to have smaller particles than tubes 1 or 2.

The results indicated that acidic or basic pH did not alter the stability of the particles.

Example 2: Preparation and In Vitro Analysis of the Binding of Anti-CEA Microparticles to Radioactive CEA Anti-CEA (carcinogenic embryonic antigen) microparticles were formed as generally described for Reaction #3 in Example 1 and described in more detail below. The resulting microparticles were then combined with various concentrations of radioactive CEA to determine whether the anti-CEA antibodies incorporated in the microparticles retained affinity for the CEA ligand.

Preparation of Anti-CEA Microparticles

A 14.3% solution of each polymer, polyvinylpyrrolidone (MW 40,000) and polyethylene glycol (MW 3500), obtained from Sigma, St. Louis, Mo., was prepared by adding 14.3 grams of polymer to 100 ml of distilled water. The pH of each 14.3% polymer solution was adjusted to a pH of approximately 6.25. The polymer solutions were mixed 1:1 to create a PVP/PEG polymer mixture.

As a control, a 0.45 ml aliquot of purified goat anti-CEA gammaglobulin was reacted with 3.6 ml of the PVP/PEG polymer mixture by vortexing while adding the polymer mixture to the gammaglobulin in the absence of glutaraldehyde. Reactants were allowed to stand at 3° C. for 30 minutes. Reactants were centrifuged at 2300 rpm for 60 minutes at 20° C. Supernatants were decanted and precipitates resuspended in 0.9 ml phosphate buffered saline.

Resuspended precipitates were washed with 1.8 ml of the polymer mixture, preadjusted to pH 6.25, allowed to stand at 3° C. for 20 minutes, and centrifuged at 5000 rpm for 30 minutes at 20° C.

0.9 ml of purified goat anti-CEA gammaglobulin was reacted with 2 ml of the PVP/PEG polymer mixture, pH 6.25 containing 20 µl glutaraldehyde by vortexing while adding the polymer mixture/glutaraldehyde to the gammaglobulin. Reactants were mixed at 20° C. for 90 minutes. Reactants were centrifuged at 2300 rpm for 60 minutes at 20° C. The supernatant was decanted and the precipitate resuspended in 1 ml phosphate buffered saline. Eighty microliters of DL-lysine was added to the resuspended precipitate and mixed. The reactants were placed at 4° C. overnight.

Reactants were centrifuged at 5000 rpm for 30 minutes at 20° C. The sample was placed at 4° C. for 60 hours and then re-centrifuged. The supernatant appeared clear and was decanted. The precipitate, containing the anti-CEA microparticles, was resuspended in 10 ml phosphate buffered saline (1X).

Binding Analysis

Radioactive CEA ($I^{125}$) was diluted with phosphate buffered saline containing 10% liquid fish gelatin. The diluted $I^{125}$CEA contained 39313 counts per 100 µl.

Ten reaction tubes, each containing 100 µl of the diluted $I^{125}$CEA, were prepared as indicated below in Table 3 by adding the appropriate volume of resuspended anti-CEA microparticles.

The radioactive CEA/anti-CEA microparticle mixtures in tubes 1–5 were incubated for 2 hours in the refrigerator while shaking. The radioactive CEA/anti-CEA microparticle mixtures in tubes 6–9 were incubated for 15 minutes at room temperature while shaking. Reactants were washed three times with phosphate buffered saline containing 10% liquid fish gelatin, centrifuged 1 minute in a high speed centrifuge, and resuspended in phosphate buffered saline. The results indicate that the anti-CEA microparticles are immunologically active and react with CEA as shown numerically in Table 3 and graphically in FIG. 1.

TABLE 3

Quantitative Analysis of the Binding of Anti-CEA Microparticles to Radioactive CEA

| Tube # | CEA Microparticles (µl) | cpm |
| --- | --- | --- |
| 1 | 0 | 105 |
| 2 | 10 | 1286 |
| 3 | 20 | 1936 |
| 4 | 40 | 2912 |
| 5 | 80 | 3406 |
| 6 | 10 | 1377 |
| 7 | 20 | 1259 |
| 8 | 40 | 2977 |
| 9 | 80 | 4715 |

Example 3: Effect of pH on the Formation of Microparticles

This experiment demonstrated the effect of pH on the ability to form IgG microparticles.

Experimental Procedure:

A polymer mixture of PVP/PEG was prepared as generally described in Example 2 (48% total polymers) and was adjusted to the pH indicated in Table 4. One milliliter of each solution was placed in each of 7 centrifuge tubes:

TABLE 4

Adjusted pH of PVP/PEG Mixture

| Tube # | pH of PVP/PEG |
| --- | --- |
| 1 | 4.6 |
| 2 | 5.2 |
| 3 | 5.8 |
| 4 | 6.6 |
| 5 | 7.4 |
| 6 | 8.1 |
| 7 | 9.2 |

100 µl of a 5.0% glutaraldehyde (Sigma, St. Louis, Mo.) solution, in deionized water, was added to each tube and mixed well.

300 µl of a 3X concentrated sample of human IgG purified from human plasma was added as described above in Example 2, while vortexing. The mixture was mixed at 20° C. for 1 hour and the material centrifuged at 3800 RPM for 30 minutes at 20° C. Supernates were decanted and the particles washed in 5 ml 0.5M glycine in 1X PBS buffer, then mixed for 60 minutes 20° C. and centrifuged at 3800 RPM for 30 minutes at 20° C. Supernates were decanted and the particles washed in 5 ml 0.5M glycine in 1X PBS.

Observations:

After the addition of the purified IgG to the tubes and mixing for 20 minutes, a trend in aggregate size was observed. As the pH of the PVP/PEG mixture increased, so did the size of aggregates formed.

First Precipitates:

As the pH of PVP/PEG mixture increased, the precipitates became smaller, more wet and orange in color. A noticeable difference in these characteristics occurred at pH 6.6.

Tube #7 had to be treated very carefully because the precipitate was not adhered to the wall of the tube. 90% of the supernate was carefully removed by a disposable pipet.

First Resuspension:

There is a direct relationship between the pH of the PVP/PEG mixture and the particle size formed. As the pH increased so did the particle size. At pH 6.6 the particles were noticeably larger than at pH 5.8.

Second Precipitates:

At pH 6.6 and higher the precipitates were not adhered to the wall of tube and slid down the side of the tube quite easily. As the pH increased the precipitates went from yellow to orange.

Second Resuspension:

Identical to first resuspension.

The particles were brought to room temperature, mixed well, and then centrifuged at 2600 RPM at 20° C. for 30 minutes. Supernatants were decanted and precipitates resuspended in 5.0 ml of 0.5M glycine in 1X PBS buffer, pH 5.6. The wash procedure was then repeated 3 more times until the supernatants were clear.

Conclusion:

As the pH of the PVP/PEG mixture decreases from 9.2 to 4.6, the size of the particles formed by the crosslinking action of glutaraldehyde became smaller and more uniform in size.

Example 4: Preparation of Enzyme-labelled Albumin Microparticles

1. Sixty milligrams of chicken egg albumin were dissolved in 2 ml of a polymer mixture of PVP/PEG prepared as described in Example 2. The pH was adjusted to 4.5 with 1N HCl. 200 µl of Cappell affinity purified rabbit anti-goat IgG horse radish peroxidase (HRP) conjugate was added.
2. The mixture was rotary turned for 30 minutes.
3. A 10% glutaraldehyde solution was diluted 1:4 and 200 µl was added to mixture.
4. The mixture was rotary turned for 30 minutes.
5. The mixture was centrifuged at 1500 rpm for 30 minutes at 20° C. and the supernatant removed.
6. The precipitate was resuspended in glycine buffer and washed 2 times by centrifuging at 1500 rpm for 10 minutes at 20° C.
7. The precipitate was resuspended in 0.15M Tris saline, pH 7.4, containing 1% fish gelatin, 2 ml total volume and contained particles.

Analysis:

1. 4 drops of HRP substrate were added to two glass tubes.
2. 4 drops of the resuspended precipitate of step 7 above were added to one tube and mixed.
3. 4 drops of the supernatant from step 5 above were added to the other glass tube and mixed.

Results:
1. The tube containing the supernatant from step 5 was clear (no color).
2. The tube containing the resuspended precipitate from step 7 was marine blue in color within 5 minutes indicating that the particles were labelled with the HRP.

Example 5: In vivo Administration of Anti-HCG Polymer Microparticles

Fluorescently-labelled anti-Human Chorionic Gonadotropin (anti-HCG) microparticles were injected into a Balb/c mouse to check clearance:

A female mouse weighing 35 grams was injected with phenobarbital for 5 minutes. The ventral cavity was surgically exposed and the aorta was injected with 100 microliters of fluorescently-labelled anti-HCG using a 27% gauge needle.

Five minutes later, 50 μl blood was removed.

Ten minutes later, 50 μl blood was removed.

It should be noted that the animal was still alive at the time of blood collection with its heart strongly beating.

The mouse was then killed by cervical dislocation.

Analysis:

1. One drop of blood (5 min and 10 min) was deposited on a glass slide having a depression for the sample and the sample was covered with a glass cover slip. One drop of oil was placed on the slip cover.
2. The blood sample was examined in a fluorescent microscope (Zeiss IIIRS) using high power.
3. Strong fluorescence was observed around cells in the 5 minute sample indicating that the microparticles were not rapidly absorbed by the animal.
4. Weak fluorescence was observed in the 10 minute sample.

Example 6: Effect of Polymer Mixture Concentration on Formation of Fluorescently-labelled Human IgG Microparticles This experiment was performed to determine the effects of the concentration of a PVP/PEG polymer mixture on the formation of antibody microparticles.

Procedure:

A volume of a PVP/PEG polymer mixture was prepared as described in Example 2 to form a polymer mixture having a polymer concentration of 53.3%, adjusted to pH 4.8. Polymer dilutions were made as set forth below in Table 5 using 0.1M sodium acetate at pH 5.0:

TABLE 5

| Volume and Percent of Polymer Mixture | | |
|---|---|---|
| Polymer Mixture (mls) | Na Acetate (mls) | Polymers % |
| 10 | 0 | 53.3% |
| 9 | 1 | 48.0% |
| 8 | 2 | 42.4% |
| 7 | 3 | 37.1% |
| 6 | 4 | 31.8% |
| 5 | 5 | 26.7% |
| 4 | 6 | 21.3% |
| 3 | 7 | 15.9% |
| 2 | 9 | 10.7% |
| 1 | 9 | 5.3% |
| 0 | 10 | 0% |

1 ml of each of the dilutions set forth in Table 5 was aliquoted into a centrifuge tube. Each tube then received 100 μl of a 5% glutaraldehyde solution prepared by adding 400 μl 25% glutaraldehyde to 2.0 ml of $H_2O$ and mixing. The polymer mixture/glutaraldehyde solutions were thoroughly vortexed.

The tubes were then reacted with 300 μl fluorescently labelled human IgG. The purified human antibody was 3X concentrated in a 0.1M glycine solution in PBS buffer at pH 11.0 and labelled with fluorescein isothiocyanate in the 0.1M glycine buffer at a concentration of 3 mg/ml. The antibody was added to the polymer mixture dilutions while vortexing, and the tubes were mixed for 1 hour followed by 30 minutes centrifugation at 2500 RPM at 20° C.

After centrifugation, the supernates were decanted and the precipitates resuspended in 5 ml of 0.5M glycine in PBS. The precipitates were broken up and shaken well. They were then centrifuged for 30 minutes at 30° C., 2500 RPM. This washing process was repeated four times.

Results:

Each tube had a different appearance from the start of the reaction. The tube containing 5.3% polymer had only slight precipitation, much of which clumped together on the walls of the tube. The tube containing 53.3% polymer had very fine particles which did not stick together or to the walls of the tube.

Overall, as the concentration of polymers increased, the precipitated matter became more fine and less sticky. The solid reacting matter in the sodium acetate control was small and sticky.

After centrifugation, the size of the precipitate was seen to increase in direct proportion to polymer concentration. The brightness of the orange color of the precipitates was inversely proportional to polymer concentration.

The control precipitate was very small and exhibited a bright orange color, as were the tubes with very low polymer concentrations. The ease with which the precipitates were broken up in the 0.5M glycine wash buffer was also related to polymer concentration. The precipitate the tube containing only 5.3% polymer mixture was sticky and difficult to break up, but in each successive tube the particles were less sticky. At a polymer concentration of 31.8% or greater, the particles separated very easily.

Following the first wash and centrifugation, a color brightness gradient still existed in the precipitates, although the difference was of a smaller magnitude. The supernates were a light orange color because fluorescein isothiocyanate was being washed out of the sample. After the third wash, the supernates were clear and the color of the precipitates was uniform. The size differences between the precipitates did not change.

Conclusion:

Polymer concentration plays a definite role in determining the characteristics of antibody particles made with the polymer mixture. Polymer concentrations of 40% and over provide very fine particles that do not stick. Also, the higher the concentration of polymers in the polymer mixture, the greater the number of antibody particles that can be formed.

Example 7: Effect of pH on Formation of Gammaglobulin Microparticles

This experiment was performed to determine the effects of polymer mixture pH on the formation of antibody particles.

Procedure:

Eight centrifuge tubes each received a 1 ml aliquot of goat serum. The serum was incubated 15 minutes with a 1.8% Triton/3% Brij (Sigma, St. Louis, Mo.) solution. This was followed by reaction with 2 mls of a 40% polymer mixture. Addition of the polymer mixture was made while vortexing and the tubes mixed for thirty minutes. The tubes were then centrifuged for 30 minutes at 3600 RPM, 20° C. The supernates were decanted and the precipitates resuspended in 1 ml 0.5M Imidazole (Baker Chemical Co.). All samples resuspended easily and clearly.

After 15 minutes incubation in the Imidazole solution, the samples received, while vortexing, 1 ml of the polymer mixture. The tubes were mixed for 30 minutes and were centrifuged for 30 minutes at 20° C., 3600 RPM. The supernates were decanted and the precipitates were resuspended easily and clearly in 1 ml deionized water. The samples are reacted with a pH gradient of the polymer mixture with pH being adjusted down with hydrochloric acid and up with 3M Imidazole. The adjusted pH values are as set forth below in Table 6:

TABLE 6

| Adjusted pH of Each Sample | |
|---|---|
| 1–4.1 | 5–7.2 |
| 2–4.8 | 6–8.0 |
| 3–5.8 | 7–8.7 |
| 4–6.6 | 8–9.3 |

1 ml of the pH adjusted polymer mixture was added to each of the tubes followed by 10 minutes of mixing. After mixing, each tube received 40 μl of 25% glutaraldehyde diluted 1:10 with deionized water. Again the tubes were mixed for 10 minutes and centrifuged for 30 minutes at 20° C., 3600 RPM. The tubes were decanted and the particles resuspended in 1 ml 1X PBS.

Results:

After centrifugation the samples showed a clear gradient in relation to pH for both size and color. Prior to resuspension in the 1X PBS, the precipitates in samples 1, 2 and 7 were slightly smaller than those in the other tubes. There was no apparent precipitate in sample of pH 9.3 because the high alkalinity inhibits the ability of the polymer mixture to precipitate proteins. The samples of acidic pH values were white, with the samples growing increasingly yellow-orange across the gradient. Also, particle size was directly proportional to pH, with the particles in sample 1 being very fine. As pH increased, the particles grew larger and tended to clump more.

Conclusion:

The size of antibody particles can easily be controlled by altering the pH of the polymer mixture. At high pH, glutaraldehyde forms very strong bonds with the amino groups of proteins, accounting for the yellow-orange color and overall stickiness of the increasingly basic samples. However, at acidic pH values the effects of the glutaraldehyde are lessened. Particles can still form but they are much more fine with less of a tendency to clump than those particles made with the basic polymer mixture.

Example 8: Effect of Glutaraldehyde Concentration on Formation of IgG Microparticles This experiment was performed to show the effect of increasing the amount of glutaraldehyde on the formation of IgG microparticles.

Experimental Procedure:

Placed 1.0 ml of the polymer mixture described in Example 2, containing 48% total polymers, pH 4.8, into 7 centrifuge tubes. Added the varying volumes of glutaraldehyde, as set forth in Table 7, to each tube:

TABLE 7

| Concentration of Glutaraldehyde per Tube | |
|---|---|
| Volume of Glutaraldehyde | Tube # |
| 2 μl | 1 |
| 5 μl | 2 |
| 10 μl | 3 |
| 20 μl | 4 |
| 50 μl | 5 |
| 100 μl | 6 |
| 200 μl | 7 |

Mixed each tube well and added 300 μl of purified IgG 3X concentrated in 0.1M glycine, pH 11.2, buffer containing 2 ng/ml fluorescein isothiocyanate (FITC) to each tube. All tubes were mixed for one hour at 20° C., then centrifuged at 3600 RPM at 20° C. for 30 minutes.

Decanted supernatants and washed particles in 5.0 ml 0.5M glycine in 1X PBS buffer, pH 7.0. Mixed for 30 minutes at 20° C. Centrifuged at 2600 RPM 20° C. for 30 minutes. This wash procedure was repeated twice more.

Particles were stored at 4° C. in 5.0 ml 0.5M glycine in 1X PBS buffer pH 7.0.

Observations:

As the amount of glutaraldehyde increased, the number of particles and a more orange color was noticed.

The particles were repeatedly washed until the supernates appeared clear.

The final centrifugation yielded pellets that were not fully adhered to the wall of the tube. The supernates had to be carefully removed with a disposable pipet and 1.0 ml of buffer was left behind.

Conclusions:

There is a direct relationship between increasing the amount of glutaraldehyde added to the polymer mixture (48% Total polymers) and an increase in the amount of particles formed. The amount of glutaraldehyde (between 2 μl and 200 μl of a 25% aqueous solution) appeared to have no effect on increasing or decreasing particle size.

Example 9: Preparation and In Vitro Analysis of the Binding of Anti-HCG Monoclonal Antibody Microparticles to Iodinated HCG This experiment was performed to form human chorionic gonadotropin (HCG) specific monoclonal antibody microparticles with a PVP/PEG polymer mixture and different concentrations of glutaraldehyde and to demonstrate the ability of the microparticles to bind HCG indicated antigens in an immunoassay.

Experimental Procedure:

Thawed out two, one ml samples of purified HCG antibody, prepared according to the methods specified in Example 2, pooled together. Mixed well. Created increasingly smaller percent solutions of glutaraldehyde (from a 25% aqueous solution) as set forth below in Table 8.

TABLE 8

Final Percent Glutaraldehyde per Tube

| Tube # | Vol. Glut. | Vol. Deionized H$_2$O | Final % Glut. |
|---|---|---|---|
| 1 | 100 µl | 0 µl | 25% |
| 2 | 50 µl | 50 µl | 12.5% |
| 3 | 25 µl | 75 µl | 6.25% |
| Diluted 25% glutaraldehyde with deionized water 1:10 | | | |
| 4 | 100 µl | 0 µl | 2.5% |
| 5 | 50 µl | 50 µl | 1.25% |
| 6 | 25 µl | 75 µl | 0.625% |
| 7 | 0 µl | 100 µl | 0% |

Added 150 µl of the pooled HCG sample to each tube containing 100 µl of the percent glutaraldehyde solutions, while vortexing. Mixed for 45 minutes at room temperature.

Added 0.5 ml of the polymer mixture (40% total polymers, pH 6.6), rapidly to each tube and mixed 30 minutes at 20° C. Centrifuged at 3500 RPM at 4° C. for 3 minutes. Decanted supernatants. Added 2 mls 0.5M glycine in 1X PBS pH 7.0 to each tube and mixed 30 minutes at 20° C. Centrifuged at 3000 RPM for 30 minutes at 4° C. Decanted supernatants and resuspended particles in 2.0 ml 0.5M glycine in 1X PBS. Mixed well but briefly. Centrifuged at 3000 RPM for 30 minutes at 4° C. Repeated wash procedure once more. Placed at 4° C. overnight.

Centrifuged particles at 3000/rpm at 4° C. for 12 minutes. Decanted supernates and resuspended particles in 2.0 ml 1X PBS.

Observations:

A trend in the size of the particles was noticed. As the glutaraldehyde concentration decreased, the number of particles decreased, but the size of the particles increased. No particles were observed in tube #7 (control).

Immunoassay:

Placed 50 µl of each sample containing the particles as prepared above into 3 sets of six tubes (A, B & C) (18 tubes in all).

Added 25 µl of HCG tracer (iodinated HCG antigen, Becton Dickinson, San Jose, Calif.) to tubes 1–6 in set A plus to a tube containing HCG antibody control for total count.

Added 25 µl of follicle stimulating hormone (FSH) tracer (iodinated FSH antigen) to tubes 1–6 in set B plus to a tube containing FSH antibody control for total counts.

Added 25 µl of Estradiol tracer (iodinated Estradiol antigen) to tubes 1–6 in set C plus to a tube containing Estradiol antibody control for total counts.

Vortexed all tubes briefly and allowed to stand 60 minutes at room temperature. Added 2.0 mls deionized water mixed and centrifuged for 30 minutes at 3000 RPM. Gently decanted tubes (approximately 100 microliters of residual water was left behind in the tubes).

All tubes were counted for 1 minute in a scintillation counter. The results are set forth below in Table 9.

TABLE 9

Binding of Radioactive Antigen to anti-HCG Microparticle

| Tube # | | |
|---|---|---|
| Set A | HCG (cpm) | |
| 1 | 7410.7 | |
| 2 | 10105.9 | |
| 3 | 12410.9 | |
| 4 | 11349.3 | |
| 5 | 7145.4 | |
| 6 | 11350.2 | |
| 7 | 21610.4 | Total counts |
| Set B | FSH | |
| 1 | 381.2 | |
| 2 | 376.9 | |
| 3 | 422.1 | |
| 4 | 467.0 | |
| 5 | 493.5 | |
| 6 | 392.3 | |
| 7 | 3157.2 | Total counts |
| Set C | Estradiol | |
| 1 | 232.7 | |
| 2 | 262.1 | |
| 3 | 225.4 | |
| 4 | 251.1 | |
| 5 | 201.3 | |
| 6 | 189.8 | |
| 7 | 1970.3 | Total counts |

Conclusion:

As the concentration of glutaraldehyde is decreased, fewer anti-HCG monoclonal antibody microparticles are formed, but these particles are larger in size. The anti-HCG microparticles are capable of binding iodinated HCG antigen in an immunoassay. The anti-HCG microparticles are not capable of nonspecific binding of other iodinated antigens such as FSH and Estradiol in an immunoassay.

Example 10: Preparation of Tetanus Toxoid Microparticles

This experiment was performed to prepare tetanus toxoid microparticles with a polymer mixture of PVP and PEG and glutaraldehyde.

Experimental Procedure:

Placed 1.0 ml of a 54% polymer mixture of PVP/PEG into two centrifuge tubes. Added 100 µl glutaraldehyde (25% aqueous solution) to one tube and 10 µl of glutaraldehyde to the other and vortexed thoroughly.

Shot 0.5 ml tetanus toxoid (1.0 mg/ml) (Dept. of Public Health) into both tubes and vortexed thoroughly.

Mixed for 4 hours and 15 min at room temperature. Centrifuged at 3000 RPM at 4° C. for 30 minutes. Decanted supernates and resuspended particles in 2.0 ml of 0.5M glycine in 1X PBS buffer. Allowed to stand overnight at 4° C.

Repeated wash procedure twice more. Particles were finally resuspended in 0.5 ml 1X PBS buffer.

Observations:

The reaction containing 100 µl glutaraldehyde contained more particles than the reaction with 10 µl glutaraldehyde. Particles for both reactions were similar in size. The particles appear very small to the eye.

Example 11: Preparation of Bovine Serum Albumin Polymer Microparticles

This experiment was performed to demonstrate the formation of bovine serum albumin (BSA) microparticles with a polymer mixture of PVP/PEG and glutaraldehyde and to observe the effect of different volumes of glutaraldehyde used in this process.

Experimental Procedure:

Placed 110 mg BSA in 11 ml of 0.1M Tris$_{TM}$ base, pH 9.0. Added 11 mg FITC, adjusted pH to 9.5 with base mixed for 30 minutes a 20° C. to form fluorescently labelled BSA.

Set up 8 tubes each with 1 ml of the polymer mixture (pH 5.0, 48% total polymers) and added the following amounts of glutaraldehyde (25% aqueous solution) as set forth in Table 10.

TABLE 10

| Concentration of Glutaraldehyde per Tube | |
| --- | --- |
| Tube # | Volume of Glutaraldehyde |
| 1 | 200 μl |
| 2 | 100 μl |
| 3 | 50 μl |
| 4 | 25 μl |
| 5 | 6 μl |
| 5 | 12 μl |
| 7 | 3 μl |
| 8 | 1 μl |

Mixed briefly but thoroughly by vortexing. Added 300 ml of BSA-FITC solution. Mixed for 7.5 hours.

Conclusions:

Bovine serum albumin microparticles were formed in each tube. As the glutaraldehyde amount decreased, larger size aggregates were formed in addition to small fine particles seen with all volumes of glutaraldehyde (1 μl to 200 μl). Also, as the glutaraldehyde amount increased the number of the small fine particles increased.

Example 12: Preparation of Immunoglobulin Microparticles with Saturated Ammonium Sulfate as the Dehydrating Agent This experiment was performed to prepare immunoglobulin microparticles using saturated ammonium sulfate, over a pH gradient, as the dehydrating agent and glutaraldehyde as the crosslinking agent.

Experimental Procedure:

Prepared 100 ml of a saturated ammonium sulfate solution by placing 76.1 g ammonium sulfate (Fisher Scientific, Pittsburgh, PA) in up to 100 ml deionized water, pH 5.2.

Solutions of saturated ammonium sulfate with differing pHs were prepared by adjusting aliquots of the solution prepared above with glacial acetic acid for low pH values and with 2N sodium hydroxide for higher pH values as set forth below in Table 11.

TABLE 11

| Adjusted pH of Saturated Ammonium Sulfate Solution per Tube | |
| --- | --- |
| pH | tube number |
| 4.2 | 1 |
| 5.2 | 2 |
| 6.5 | 3 |
| 7.1 | 4 |
| 8.1 | 5 |
| 9.2 | 6 |

A 0.3 ml aliquot of each saturated ammonium sulfate solution was placed into a 15 ml centrifuge tube.

50 ml of glutaraldehyde (25% aqueous solution) was added to each tube and mixed well.

A 0.3 ml sample of purified IgG from human plasma, purified using the methods set forth in Example 2) was added to each tube. All tubes were then mixed for about 15 minutes at room temperature. The formation of particles was observed immediately after the addition of the purified IgG samples.

5.0 ml of a 0.5M glycine in 1X PBS buffer, pH 7.0, was added to each tube. Mixed tubes well and then centrifuged at 2600 RPM at 20° C. for 30 minutes.

Decanted supernatant and washed particles in 5.0 mls 0.5M glycine in 1X PBS buffer, pH 7.0. Mixed for 30 minutes at 20° C. and then centrifuged at 2600 RPM at 20° C. for 30 minutes. This wash procedure was repeated three more times.

Observations:

Immediately after purified IgG was added to the ammonium sulfate (saturated) solutions containing glutaraldehyde, particles were observed upon mixing of the tubes.

A direct relationship was found between the increase in the pH of the saturated ammonium sulfate solution and an increase in the amount of particles formed.

The size of the particles did not differ between the range of pHs of the saturated ammonium sulfate solutions.

Example 13: Preparation of Immunoglobulin Microparticles with a Mixture of Saturated Ammonium Sulfate and Polyethylene Glycol as the Dehydrating Agent This experiment was performed to prepare immunoglobulin microparticles using a mixture of saturated ammonium sulfate and polyethylene glycol (PEG) as the dehydrating agent and glutaraldehyde as the crosslinking agent.

Experimental Procedure:

A 100 ml volume of a saturated ammonium sulfate solution was prepared as described in Example 12. A 20% solution of polyethylene glycol (Sigma, St. Louis, Mo.) in 0.1M sodium acetate, pH 4.8 was also prepared. The ammonium sulfate solution was added, in small increments, to 10 ml of the PEG solution until the ammonium sulfate precipitated. The largest volume of ammonium sulfate that would stay in solution was 1.2 ml. One ml of this ammonium sulfate/PEG solution was aliquoted into each of eight tubes. The tubes then received 25% glutaraldehyde (Sigma, St. Louis, Mo.) in the amounts specified in Table 12 below

TABLE 12

| Amount of Glutaraldehyde Added to Ammonium Sulfate/PEG Solution | |
| --- | --- |
| Tube number | Glutaralehyde |
| 1 | 0 μl |
| 2 | 2 μl |
| 3 | 5 μl |
| 4 | 10 μl |
| 5 | 20 μl |
| 6 | 50 μl |
| 7 | 100 μl |
| 8 | 200 μl |

Tubes 5–8 displayed a color reaction that increased in strength across the gradient. The brightness of the color also increased over time. This was a result of the glutaraldehyde reacting with the amines of the ammonium sulfate. Tubes 1–4 did not change color because the glutaraldehyde concentrations in these tubes were very low.

A 300 µl aliquot of 3 times concentrated purified porcine IgG antibody was added to each tube while vortexing. The tubes then were mixed for 60 minutes and were centrifuged for 30 minutes at 3600 RPM at 20° C.

The supernatants were decanted and 10 ml of 0.5M glycine (Sigma, St. Louis, Mo.), pH 7.0, in phosphate buffered saline, was added to each precipitate. The tubes were shaken well to break up the precipitate and stored overnight at 4° C.

The following morning, the tubes were centrifuged for 30 minutes at 3600 RPM at 20° C. The supernatants were decanted and the precipitates washed with 5 ml of the 0.5M glycine buffer solution. After shaking well, the tubes were centrifuged for 30 minutes at 3600 RPM at 20° C. Following centrifugation, the supernatants were decanted and the precipitates received 5 ml of the 0.5M glycine buffer. The tubes were shaken well.

Results:

Following the first centrifugation, the precipitates differed in size and color, with the precipitates growing larger and darker as the glutaraldehyde concentration increased. After breaking up the precipitates and mixing well, particles were apparent in all tubes except tube #1, which received no glutaraldehyde. There were fine particles that appeared to be of uniform size in tubes 2–7. However, the particles were sticky and tended to clump in all tubes. There appeared to be a greater proportion of clumping relative to the amount of particles in the tube in those tubes that received less than 20 µl glutaraldehyde. These results were consistent over the final two washes.

Example 14: Preparation of Insulin Microparticles

This experiment was performed to prepare insulin microparticles with a polymer mixture of PVP and PEG and glutaraldehyde, measure the concentration of microparticles formed, and assay their immunologic activity.

Preparation of Microparticles:

Placed 30 mg insulin (Sigma Chemical Co., St. Louis, Mo.) from bovine pancreas into 3.0 ml of 3M HCl to solubilize the dessicated insulin. Adjusted pH to between 8.4 and 9.0 using 25 µl increments of 2N NaOH.

Placed a 1.0 ml aliquot of a 54% polymer mixture of PVP/PEG, pH 5.0, into three centrifuge tubes. Added the following amounts of glutaraldehyde (Grade II, 25% aqueous solution, Sigma Chemical Co., St. Louis, Mo.) to each tube: 25 µl glutaraldehyde in tube A, 50 µl glutaraldehyde in tube B, 100 µl glutaraldehyde in tube C.

Added 1.0 ml of the solubilized insulin to each tube while vortexing. Mixed for 6–8 hours at 20° C. and allowed to stand overnight.

Washed particles nine times using 5.0 ml of lysine solution, pH 9.4, containing 1 mg/ml sodium azide (10 mg lysine/ml deionized water). The washing procedure consisted of adding 5.0 ml lysine solution to the particles, mixing well but briefly. Centrifuged at 2300 rpms for 30 minutes at 20° C. Aspirated supernatant and repeated the process. Stored particles in the lysine solution overnight at 4° C.

Centrifuged particles, aspirated supernatant, and resuspended particles in 5.0 ml of a 1X phosphate buffered saline solution, pH 7.0. The pH of each resuspension was as follows: tube A was pH 9.2, tube B was pH 9.2, and tube C was pH 8.8.

Centrifuged particles, aspirated supernatant, and resuspended particles in 5.0 ml of a 1X phosphate buffered saline solution, pH 7.0. The pH of each resuspension was as follows: tube A was pH 8.0, tube B was pH 7.4, and tube C was pH 7.2.

Centrifuged particles, aspirated supernatant, and resuspended particles in 5.0 ml of a 1X phosphate buffered saline solution, pH 7.0. The final pH of each resuspension was as follows: tube A was pH 7.4, tube B was pH 7.2, tube C was pH 7.2.

Results:

The particles formed were very small and fine. During centrifugation in the lysine solution, the particles were unable to fully compact. After washing with the phosphate buffered saline solution, particles were able to compact to a greater degree and also formed aggregates of particles.

Tube C had the largest amount of particles. Tube B had more particles than Tube A. Therefore, particle formation increased with the amount of glutaraldehyde added to each tube.

Sheep Anti-insulin Peroxidase Assay

The immunologic activity of the insulin microparticles was determined by measuring the ability of the microparticles to bind anti-sheep insulin in a sheep anti-insulin peroxidase assay.

Three series of four tubes each were set up. Placed the following volumes of insulin particles from each of Tubes A, B and C above into the appropriate tube for each series as shown below in Table 13.

Added the appropriate amount of 1X phosphate buffered saline, pH 7.0, to each tube to achieve a final volume of 1.0 ml. Mixed all tubes well, but briefly. Added 100 µl of sheep anti-insulin peroxidase (Biodesign International, Kennebunkport, Me., 5 mg/ml protein). Mixed well. Incubated tubes at room temperature for 4 hours and ten minutes. Placed tubes at 4° C. overnight.

Centrifuged all tubes in all series at 3000 rpm at 20° C. for 30 minutes. Carefully removed only 90% of the supernatant to prevent accidental loss of particles. Added 1.0 ml of 0.2% Tween™ detergent in 1X phosphate buffered saline to aspirated tubes, and mixed by vortexing. Reacted 100 µl of each supernatant with 0.5 ml the chromogen TM Blue™ (tetramethylbenezidine, Center for Diagnostic Products, Milford, Mass.). All supernatants were positive. Repeated this entire wash procedure twice more to remove all excess, unbound sheep anti-insulin peroxidase.

After the final wash, 90% of the supernatant was aspirated, and 50 µl of particles removed from each tube and reacted with 0.2 ml the TM Blue™ chromogen.

Results

The results, shown below in Table 13, demonstrate that the insulin microparticles are capable of binding anti-sheep insulin, which indicates that these particles are immunologically active.

TABLE 13

Ability of Insulin Particle Formed Using
Various Amounts of Glutaraldehyde to Bind
Anti-sheep Insulin

| Insulin Particles | glutaraldehyde | | |
|---|---|---|---|
| (vol.) | 25 µl | 50 µl | 100 µl |
| 100 µl | ++++++++ | +++++++ | +++++ |
| 50 µl | +++++++ | +++++ | ++++ |
| 20 µl | +++++ | +++ | ++ |
| 10 µl | +++ | ++ | + |

Inhibition Assay

The immunologic activity of the insulin microparticles was determined by measuring the ability of the microparticles to bind anti-sheep insulin in an inhibition assay.

Two series of 5 tubes each were prepared as follows. Placed the following volumes of insulin particles, from reactions A and C above, into the appropriate centrifuge tubes as shown below in Table 14.

Added 100 µl Immunophase Insulin Tracer™ (iodinated insulin, Ciba Corning) to all tubes in both series. Vortexed. Added 1.0 µl Immunophase™ insulin antibody (Ciba Corning). Vortexed. Allowed to stand for 4 hours and 30 minutes at room temperature. Centrifuged at 3000 rpms for 30 minutes at 20° C.

Counted tubes in scintillation gamma counter for one minute.

Results

The results, shown below in Table 14, demonstrate, using an inhibition assay, that the insulin microparticles are capable of binding anti-sheep insulin, which indicates that these particles are immunologically active.

TABLE 14

Ability of Insulin Particle Formed Using
Various Amounts of Glutaraldehyde to Bind
Anti-sheep Insulin in the Presence of
Radioactive Insulin

| Insulin Particles | cpm | |
|---|---|---|
| (vol.) | Reaction A | Reaciton B |
| 100 µl | 4235.5 | 1266.0 |
| 50 µl | 1460.1 | 1594.5 |
| 25 µl | 1573.6 | 1724.0 |
| 10 µl | 1958.4 | 2291.6 |
| 0 µl | 3192.6 | 3119.6 |

Example 15: Immunization of Mice with Tetanus Toxoid Microparticles

This experiment was performed to determine the in vivo effects of immunization with tetanus toxoid microparticles.

The procedures, results and conclusions of the experiment are as follows:

Procedures

Tetanus toxoid microparticles were prepared as generally described above in Example 10 as follows:

A 27% solution of each polymer, polyvinylpyrrolidone (MW 40,000) and polyethylene glycol (MW 3500), obtained from Sigma, St. Louis, Mo., was prepared by adding 27 grams of polymer to 100 ml of distilled water. The pH of each polymer solution was adjusted to a pH of approximately 6.25. The polymer solutions were mixed 1:1 to create a PVP/PEG polymer mixture (54% total polymers).

100 µl of a 5.0% glutaraldehyde (Sigma, St. Louis, Mo.) solution, in deionized water, was added to 1.0 ml of the PVP/PEG polymer mixture and vortexed thoroughly.

0.5 ml of tetanus toxoid (1.0 mg/ml), obtained from the Dept. of Public Health were added to the PVP/PEG-glutaraldehyde mixture and vortexed thoroughly.

The combination was mixed for 4 hours and 15 minutes at room temperature and then centrifuged at 3000 RPM at 4° C. for 30 minutes. Supernatants were decanted, particles resuspended in 2.0 ml of 0.5M glycine in 1X PBS buffer and allowed to stand overnight at 4° C.

The wash procedure was repeated twice more. Tetanus toxoid particles were finally resuspended in 0.5 ml 1X PBS buffer. The particles had a particle size of between approximately 50 and 100 microns.

A group of thirty-two mice were each injected subcutaneously, following FDA protocol, with a primary dose containing 2 µg of the tetanus toxoid particles. A secondary injection containing 2 µg of the tetanus toxoid particles was administered seven weeks after the primary injection. Blood samples were taken from the mice at 2, 4, 5, 8, and 10 weeks after primary injection and antibody titers in the blood were determined by immunoassay. Mice were challenged with a lethal dose of tetanus toxoid fourteen weeks after the primary injection.

Results

As shown FIG. 2, antibody titers increased from approximately 10, at 4 weeks after primary injection, to approximately 3000, at 10 weeks after primary injection. The dotted line indicates titers conferring 2 antitoxin units of protection from tetanus toxoid. Titers above the dotted line indicate a positive immune response, according to FDA standards. Therefore, as shown in the FIG. 2, the mice had a positive immune response as early as four weeks after injection with the tetanus toxoid microparticles. The increase in antibody titer from four to ten weeks indicates that the microparticles may be providing slow release of the tetanus toxoid antigen.

100% of the mice survived after challenge with the lethal dose of tetanus toxoid administered at fourteen weeks. This survival rate indicates a strong immune response conferring protection against tetanus toxoid.

At the conclusion of the experiment, all of the mice appeared healthy. There was no noticeable inflammation or scarring at the site of injection and no significant weight loss after innoculation. Therefore, the tetanus toxoid microparticles were generally non-toxic when administered subcutaneously.

This experiment provides in vivo data showing that administration of tetanus toxoid microparticles, prepared in accordance with the method described above, provides a slow release of tetanus toxoid antigen, causes a positive immune response, and protects against lethal challenge by tetanus toxoid in the absence of adverse effects.

Example 16: Preparation of Albumin Microparticles Using Linear Polymers and Heat This experiment was performed to prepare albumin microparticles by incubating albumin with polymer mixtures of PVP and PEG at various temperatures.

Experimental Procedure:

Placed into each of four reaction tubes 1.0 ml of a bovine serum albumin-FITC solution containing 1% bovine serum albumin (BSA) plus 10 µl dialyzed fluorescein isothiocyanate (FITC) albumin. Added 2.0 ml of a polymer mixture containing 8.0% PVP and 20% PEG in 0.1M sodium acetate, pH 5.0 to each tube while vortexing.

Reaction 1 was mixed at room temperature for 1.5 hours. Reaction 2 was mixed at room temperature for 30 minutes, then incubated in a 58° C. water bath for 30 minutes. Reaction 3 was immediately placed in a 58° C. water bath for 30 minutes. Reaction 4 was mixed at room temperature for 30 minutes, then incubated in a 37° C. water bath for 30 minutes, then incubated in a 58° C. water bath for 30 minutes.

Added 2.0 ml 10% ethanol to each reaction mixture and mixed briefly. Centrifuged for 30 minutes at 3000 rpm at 20° C. Carefully aspirated supernatants. Resuspended precipitants in 2.0 ml ethanol. Reaction mixture 1 was clear while 2–4 were cloudy. Centrifuged and resuspended in 2.0 ml deionized water and examined under fluorescent microscope.

Results

No microparticles were found in reaction mixture 1. Reaction mixture 2 contained non-aggregated microparticles approximately 1–10 µm in diameter. Reaction mixture 3 contained non-aggregated microparticles approximately 10 µm in diameter with many microparticles less than 1 µm in diameter. Reaction mixture 4 contained non-aggregated microparticles approximately 10–25 µm in diameter with some microparticles less than 1 µm in diameter.

Experimental Procedure:

Placed into each of two series of six reaction tubes 1.0 ml of a bovine serum albumin-FITC solution containing 1% bovine serum albumin (BSA) plus 10 nl dialyzed fluorescein isothiocyanate (FITC) albumin. Added 0.5 ml, 1.0 ml, 2.0 ml, 3.0 ml, 4.0 ml, or 5.0 ml of a polymer mixture containing 8.0% PVP (MW 90,000) and 20% PEG (MW 3350), pH 5.0, to each tube in the Series A while vortexing. Added 0.5 ml, 1.0 ml, 2.0 ml, 3.0 ml, 4.0 ml, or 5.0 ml of a polymer mixture containing 20% PVP (MW 40,000) and 20% PEG (MW 3350), pH 5.0, to each tube in Series B while vortexing.

Allowed reaction mixtures to stand for 30 minutes at room temperature, then placed tubes in a 37°–40° C. water bath for 30 minutes, then transferred tubes to a 56°–60° C. water bath for 30 minutes. Added 2 ml of 10% ethanol and centrifuged at 3000 rpm for 30 minutes at room temperature. Aspirated supernatants and resuspended microparticles in 2.0 ml of 10% ethanol. Centrifuged again for 15 minutes, resuspended in 2.0 ml deionized water and examined under fluorescent microscope.

Results

Series A (8 0% PVP/20% PEG)

The microparticles formed using 0.5 ml of polymer mixture were mostly uniform, having a diameter range of 1–3 µm. Small clusters were observed. A few large microparticles were seen having a diameter of approximately 25 µm.

The microparticles formed using 1.0 ml of polymer mixture were less uniform than those formed using 0.5 ml, having a diameter range of <1–10 µm. Fewer clusters were observed than above. No large microparticles were seen.

The microparticles formed using 2.0 ml of polymer mixture were less uniform than those formed using 0.5 ml, having a diameter range of <1–15 µm. Very few clusters were observed. No large microparticles were seen.

The microparticles formed using 3.0 ml of polymer mixture were less uniform than those formed using 0.5 ml, having a diameter range of <1–20 µm. Very few clusters were observed. No large microparticles were seen.

The microparticles formed using 4.0 ml of polymer mixture were less uniform than those formed using 0.5 ml, having a diameter range of <1–25 µm. No clusters or large microparticles were observed.

The microparticles formed using 5.0 ml of polymer mixture were less uniform than those formed using 0.5 ml, having a diameter range of <1–30 µm. No clusters or large microparticles were observed.

Series B (20% PVP/20% PEG)

The microparticles formed using 0.5 ml of polymer mixture were in the form of small aggregates containing 10–20 microparticles each having a diameter of <1 µm. Some large microparticles were observed having a diameter of approximately 5–20 µm.

The microparticles formed using 1.0 ml of polymer mixture were in the form of small aggregates containing 10–20 microparticles each having a diameter of <1 µm. Large microparticles having a diameter of approximately 5–50 µm were frequently observed.

The microparticles formed using 2.0 ml of polymer mixture were in the form of large aggregates containing microparticles that were submicron in diameter. Some microparticles having a diameter of 1–10 µm were observed.

The microparticles formed using 3.0 ml of polymer mixture were in the form of large and small aggregates. Occasionally, individual microparticles having a diameter of approximately 5 µm were seen.

The microparticles formed using 4.0 ml of polymer mixture were in the form of small aggregates containing 10–20 microparticles each having a diameter smaller than those observed when 0.5 ml of polymer mixture was used. No individual microparticles were observed.

The microparticles formed using 5.0 ml of polymer mixture were in the form of small and large aggregates containing very small microparticles. No individual microparticles were observed.

Experimental Procedure:

Placed into each of seven reaction tubes 1.0 ml of a bovine serum albumin-FITC solution. Added 0.5 ml, 0.75 ml, 1.0 ml, 1.25 ml, 1.5 ml, 1.75 ml, or 2.0 ml of a polymer mixture containing 20% PVP (MW 40,000) and 20% PEG (MW 3350) in 0.1M sodium acetate, pH 5.0, to each tube while vortexing.

Allowed reaction mixtures to stand for 30 minutes at room temperature, then placed tubes in a 37°–40° C. water bath for 30 minutes, then transferred tubes to a 56°–60° C. water bath for 30 minutes. Added 2 ml of 10% ethanol and centrifuged at 3000 rpm for 30 minutes at 20° C. Aspirated supernatants and resuspended microparticles in 2.0 ml of 10% ethanol. Centrifuged again for 15 minutes, resuspended in 2.0 ml deionized water and examined under a fluorescent microscope.

Results

The microparticles formed using 0.5 ml of polymer mixture were in the form of small aggregates of tiny microparticles <1 µm in diameter with approximately 10–20 per aggregate. Occasionally, larger single microparticles having a diameter of 1–10 µm were observed.

The microparticles formed using 0.75 ml of polymer mixture were in the form of small aggregates with approximately 1–10 microparticles per aggregate. Occasionally, larger single microparticles having a diameter of 1–10 μm were observed.

The microparticles formed using 1.0 ml of polymer mixture formed large adherant aggregates during the 37°–40° C. incubation. The aggregates contained approximately 1–5 microparticles per aggregate. Occasionally, larger single microparticles having a diameter of 1–10 μm were observed.

The microparticles formed using 1.25 ml of polymer mixture formed aggregates during the 56°–60° C. incubation. The aggregates contained approximately 1–5 microparticles per aggregate. Occasionally, larger single microparticles having a diameter of 1–10 μm were observed.

The microparticles formed using 1.5 ml of polymer mixture formed aggregates during the 56°–60° C. incubation. The aggregates contained approximately 1–5 microparticles per aggregate. Several larger, single microparticles having a diameter of 1–10 μm were observed.

The microparticles formed using 1.75 ml of polymer mixture formed during the 56°–60° C. incubation. Due to their small size, it was difficult to determine whether the microparticles were present as aggregates. Several larger, single microparticles having a diameter of 1–10 μm were observed.

The microparticles formed using 2.0 ml of polymer mixture formed large aggregates of 10–100 microparticles per aggregate. Some single microparticles having a diameter of 1 μm were observed.

This experiment demonstrated that albumin microparticles could be prepared by incubating albumin and a PVP/PEG mixture at a temperature between 37° C. and 60° C. for approximately 30 minutes. The size of the microparticles and degree of aggregate formation could be changed by altering the composition or volume of the PVP/PEG polymer mixture added to the albumin.

Modifications and variations of the present microparticle compositions and methods of production and use will be obvious to those skilled in the art from the foregoing detailed description. Such modifications and variations are intended to come within the scope of the appended claims.

I claim:

1. A method for making microparticles having uniform size comprising the steps of:
   a) combining a solution containing a macromolecule with a solution containing both polyvinylpyrrolidone and polyethylene glycol to produce a reaction solution:
   b) incubating the reaction solution at a predetermined temperature greater than room temperature for a sufficient amount of time to form microparticles; and
   c) separating the microparticles from the reaction solution.

2. The method of claim 1 wherein the incubation temperature is greater than or equal to 37° C. and less than or equal to 80° C.

3. The method of claim 1 wherein the reaction solution is incubated for between 5 minutes and 24 hours.

4. The method of claim 1 wherein the incubation step is performed at a pH between approximately 5 and 8.

5. The method of claim 1 wherein the polyvinylpyrrolidone has a molecular weight of approximately 40,000 and the polyethylene glycol has a molecular weight of approximately 3500 and wherein the concentration of each is between 1 and 40 g/100 ml.

6. The method of claim 1 wherein the macromolecule is selected from the group consisting of a protein, carbohydrate, polysaccharide, nucleic acid molecule, virus, virus particle, pharmaceutical drug, and mixtures thereof.

7. The method of claim 1 wherein the reaction solution of step a) further comprises a crosslinking agent.

8. The method of claim 7 further comprising the step of washing the microparticles with a buffer. which contains a quenching reagent.

9. The method of claim 7 wherein the crosslinking agent is selected from the group consisting of dialdehydes, amines, multivalent ions, N-substituted maleimides, bifunctional alkyl halides, aryl halides, isocyanates, aliphatic or aromatic dicarboxylic acids, aliphatic or aromatic disulphonic acids, bifunctional imidoesters, and vinylsulphones.

10. Microparticles prepared by the method of
   a) combining a solution containing a macromolecule with a solution containing both polyvinylpyrrolidone and polyethylene glycol to produce a reaction solution;
   b) incubating the reaction solution at a predetermined temperature greater than room temperature for a sufficient amount of time to form microparticles; and
   c) separating the microparticles from the reaction solution.

11. The microparticles of claim 10 wherein the microparticles have a size between 1 and 10 microns.

12. The microparticles of claim 10 wherein the incubation temperature is greater than or equal to 37° C. and less than or equal to 80° C.

13. The microparticles of claim 10 wherein the reaction solution is incubated for between 5 minutes and 24 hours.

14. The microparticles of claim 10 wherein the incubation step is performed at a pH between approximately 5 and 8.

15. The microparticles of claim 10 wherein the polyvinylpyrrolidone has a molecular weight of approximately 40,000 and the polyethylene glycol has a molecular weight of approximately 3500 and wherein the concentration of each is between 1 and 40 g/100 ml.

16. The microparticles of claim 10 wherein the macromolecule is selected from the group consisting of a protein, carbohydrate, polysaccharide, nucleic acid molecule, virus, virus particle, pharmaceutical drug, and mixtures thereof.

17. The microparticles of claim 10 wherein the reaction solution of step a) further comprises a crosslinking agent.

18. The microparticles of claim 17 wherein the crosslinking agent is selected from the group consisting of dialdehydes, amines, multivalent ions, N-substituted maleimides, bifunctional alkyl halides, aryl halides, isocyanates, aliphatic or aromatic dicarboxylic acids, aliphatic or aromatic disulphonic acids, bifunctional imidoesters, and vinylsulphones.

* * * * *

UNITED STATES PATENT AND TRADEMARK OFFICE
CERTIFICATE OF CORRECTION

PATENT NO. : 5,578,709

DATED : November 26, 1996

INVENTOR(S) : James E. Woiszwillo

It is certified that error appears in the above-identified patent and that said Letters Patent is hereby corrected as shown below:

Col. 13, Line 10: Delete "42 C." and insert --4° C-- in place thereof

Col. 17, Line 17: Delete "27% gauge" and insert --27 $\frac{1}{2}$ gauge-- in place thereof Col. 29, Line 52: Delete "8   0%" and insert --8.0%-- in place thereof

IN THE CLAIMS:

Col. 31, Line 42: Delete "having uniform size"

Signed and Sealed this

Ninth Day of December, 1997

Attest:

BRUCE LEHMAN

Attesting Officer

Commissioner of Patents and Trademarks